(12) United States Patent
Schmitt

(10) Patent No.: US 7,359,482 B2
(45) Date of Patent: Apr. 15, 2008

(54) X-RAY DETECTOR SYSTEM

(75) Inventor: Thomas Schmitt, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 15 days.

(21) Appl. No.: 11/238,057

(22) Filed: Sep. 29, 2005

(65) Prior Publication Data

US 2006/0067474 A1 Mar. 30, 2006

(30) Foreign Application Priority Data

Sep. 30, 2004 (DE) .................... 10 2004 048 215

(51) Int. Cl.
*H05G 1/64* (2006.01)
(52) U.S. Cl. ....................... 378/98.8; 378/97
(58) Field of Classification Search ............... 378/98.8, 378/102, 108, 19, 96, 97, 116; 250/370.08, 250/370.09, 370.11, 374
See application file for complete search history.

(56) References Cited

U.S. PATENT DOCUMENTS

| | | | |
|---|---|---|---|
| 4,230,944 A | 10/1980 | Wiegman et al. ........... 250/355 |
| 4,563,586 A | 1/1986 | Jordan ........................ 250/374 |
| 4,859,855 A * | 8/1989 | Vlasbloem ................ 250/385.1 |
| 5,767,518 A | 6/1998 | Samiotes et al. ....... 250/370.13 |
| 5,877,501 A * | 3/1999 | Ivan et al. ............. 250/370.09 |
| 6,442,238 B2 * | 8/2002 | Meulenbrugge ........... 378/98.8 |
| 2005/0105688 A1* | 5/2005 | Spahn ....................... 378/98.8 |
| 2005/0213706 A1* | 9/2005 | Raymond et al. ............. 378/97 |

FOREIGN PATENT DOCUMENTS

DE 102 39 804 A1 3/2004

OTHER PUBLICATIONS

German Office Action (dated Jan. 25, 2007) for counterpart German Patent application No. 10 2004 048 215.2-52.

* cited by examiner

*Primary Examiner*—Courtney Thomas
(74) *Attorney, Agent, or Firm*—Harness, Dickey & Pierce, P.L.C.

(57) ABSTRACT

A mobile X-ray detector system is disclosed including a mobile X-ray detector and a mobile dosimeter arranged on the X-ray detector, at least during operation. Furthermore, an X-ray facility is disclosed for cooperating with such an X-ray detector system, an X-ray system including such an X-ray facility, and a corresponding X-ray detector system, as well as a mobile dosimeter and a mobile X-ray detector for constructing such an X-ray detector system.

17 Claims, 2 Drawing Sheets

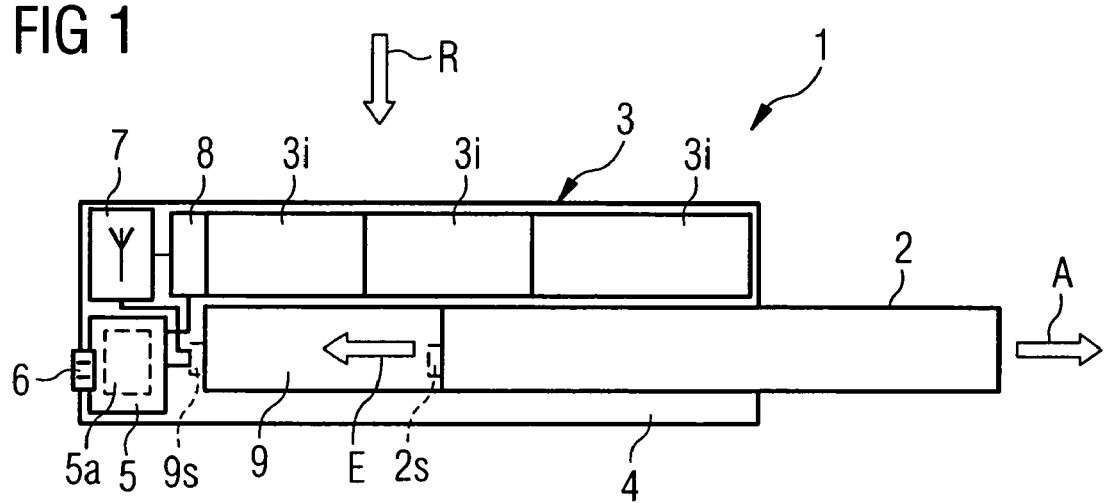
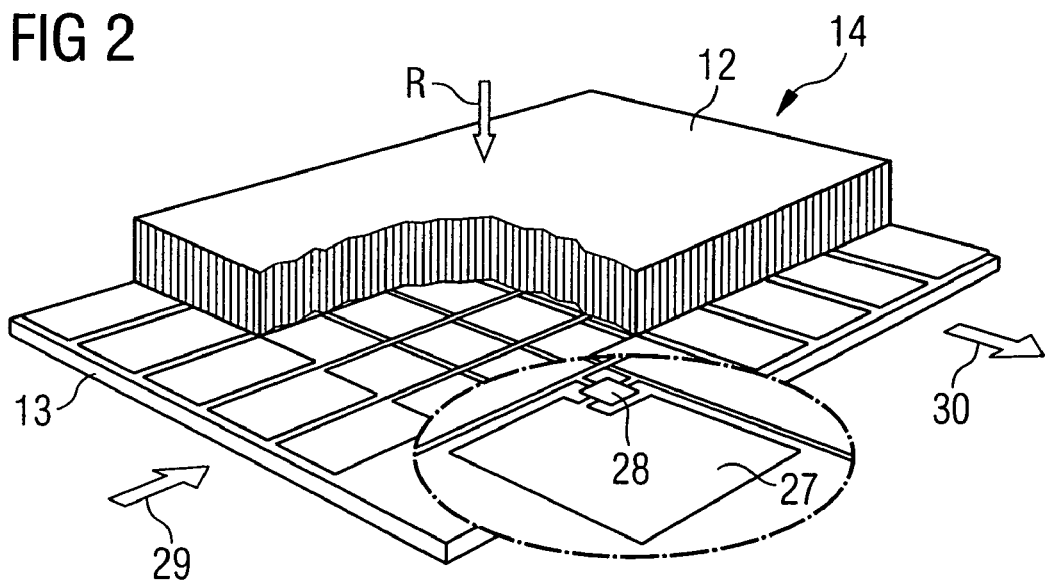

X-RAY DETECTOR SYSTEM

The present application hereby claims priority under 35 U.S.C. §119 on German patent application number DE 10 2004 048 215.2 filed Sep. 30, 2004, the entire contents of which is hereby incorporated herein by reference.

FIELD

The invention generally relates to a mobile X-ray detector system.

BACKGROUND

In most X-ray installations, the X-ray detector is coupled to other components of the X-ray installation. Thus, in the case of overtable systems, for example, the X-ray detector is located inside a patient positioning table and can be moved there in various directions below the table surface.

In facilities where the patient is X-rayed while standing, the X-ray detector is generally located in or on an appropriate wall stand. In undertable systems, the X-ray detector is suspended from a ceiling stand fastened above the patient positioning table such that it can be positioned at a suitable point above the patient positioning table. In the case of these systems, the X-ray source is likewise arranged on a suitable stand or is located in the case of an undertable system below the patient positioning table so that the X-ray source can always be positioned in an appropriate fashion relative to the X-ray detector and to the examination object so that the region of the examination object to be recorded is located in the beam path between the X-ray source and X-ray detector.

Moreover, there are, for example, so-called "C arm units" where an X-ray source is arranged on one end of a C-shaped support that can pivot about the patient. Here, the X-ray detector is arranged in opposite fashion on the other end of the C-shaped support.

However, there are also mobile X-ray detectors in addition to these stationary systems. A classic example of this is a film/foil detector or a storage foil detector. Such a mobile X-ray detector is not connected to other components of the X-ray system in any way and can be positioned at will by the user.

Such detectors are used, for example, whenever it is impossible, or possible only with difficulty, to transport the patient to the X-ray unit or to reposition him/her on a patient positioning table for example when he/she is under intensive medical care. In this case, the mobile X-ray detector is, if appropriate, positioned in the patient's bed at the appropriate point, and an X-ray source, fastened on a moveable stand, with an x-ray generator is arranged in an appropriate fashion relative to the region to be examined and relative to the X-ray detector. Then an X-ray picture is taken in situ.

It must be ensured with all X-ray detectors that the desired pictures are respectively taken with a specific dose, in order on the one hand to keep the radiation burden on the patient minimal as far as possible, and on the other hand to obtain an X-ray image of optimum mean optical density. As a rule, use is made for this purpose of a dose regulating device or a so-called automatic exposure control (AEC) that determines the incoming dose and switches off the X-radiation once a specific dose has been reached.

In this case, dose measuring elements are used that measure the X-ray dose rate incident at the X-ray detector. A signal that is proportional to the dose respectively impinging is obtained by integrating this X-ray dose rate over the recording time.

Various types of sensor can be used as dosimeter. It is, for example, customary to use ionization chambers. A current proportional to the dose rate is generated in an ionization chamber by the X-radiation in an air capacitor charged with 300 000 V, for example. Such ionization chambers are classically arranged, inter alia, upstream of a film/foil detector.

Further sensors suitable as dose measuring element are so-called semiconductor radiation receivers. Such a semiconductor radiation receiver is not transparent to radiation, and is therefore used downstream of the detector. Alternatively, it is also possible to use photomultipliers, electron multiplier elements or photodiodes that indirectly measure the dose rate via the optical brightness of an image intensifying output screen.

The dosimeters are permanently installed in the X-ray facilities, specifically in such a way that the X-ray detector is arranged downstream or upstream of the dose measuring element in accordance with the type of X-ray detector and the type of dose measuring element. Thus, for example, the dosimeter is integrated on a C arm unit at the appropriate end of the C support, directly in the housing of the X-ray detector.

The same holds, for example, for X-ray detectors suspended from ceiling stands, or X-ray undertable systems. In the case of overtable systems or systems with a wall stand, an appropriate automatic exposure control in the form, for example, of a so-called "catapult Bucky table", is permanently installed in the patient positioning table or in the wall stand.

When use is made of film/foil cassettes, the latter can be pushed into the catapult Bucky table such that they are arranged in an appropriate fashion relative to the dosimeter, that is to say directly upstream or downstream of the dosimeter depending on the type of the dosimeter in the beam path. The dosimeter is connected via control and data cables inside the table or stand to a control unit in which the signal measured by the dosimeter is then appropriately integrated in order to detect the dose respectively currently impinging, and to switch off the X-ray machine at the correct point in time.

These automatic exposure controls cannot be used when mobile detectors are used. Consequently, such recordings must be carried out in the form of a so-called "free exposure". Here, the user must work out in advance the exposure time after which the correct dose has approximately been reached, and must then ensure that the X-ray machine is switched off appropriately under time control. The operator requires considerable experience to calculate or estimate the correct exposure time. Faulty exposures therefore frequently arise with such free exposures, and so recordings have to be repeated. This leads to a higher radiation burden on the patients, and to unnecessary consumption of material.

SUMMARY

An object of at least one embodiment of the present invention is to provide a mobile X-ray detector system with the aid of which this problem is reduced or even avoided.

An object may be achieved by at least one of a mobile X-ray detector system, an X-ray facility, an X-ray system, a mobile dosimeter and/or a mobile X-ray detector.

According to an embodiment of the invention, in addition to a mobile X-ray detector, the mobile X-ray detector system also has a mobile dosimeter arranged on the X-ray detector at least during operation. This dosimeter can be connected to the X-ray detector to form a permanent unit, that is to say the dosimeter and the X-ray detector are integrated in a common housing. Alternatively, the dosimeter can, however, also be detachably coupled to the X-ray detector.

The X-ray detector system advantageously has an interface for wireless data communication with a control unit. Via the data communications interface, it is then possible to transmit the dose rate values to the control unit, which integrates the values in order to determine the current dose. Likewise, however, it would also be possible for there already to be integrated in the mobile dosimeter a control unit that carries out the integration there such that the dose values or, when a prescribed dose limiting value is reached, an appropriate signal is sent directly to the control unit. Likewise, the X-ray detector system advantageously has an integrated energy supply device.

As an alternative to a wireless interface and/or internal energy supply device, a relatively flexible cable connection for data communication and/or energy supply would also be feasible in some cases.

If the dosimeter is detachably coupled to the X-ray detector, the interface or the energy supply device can be both part of the dosimeter and part of the X-ray detector to the extent that the type of X-ray detector used has any need for a data communications interface and an energy supply device. The coupling device for coupling the dosimeter to the X-ray detector can then have appropriate contacts such that the two components can access one and the same data communications interface or energy supply device. It is also possible in principle—to the extent required—for the dosimeter and the X-ray detector to have dedicated data communications interfaces and energy supply devices.

The energy supply device, in at least one embodiment, may also include a rechargeable battery. The X-ray detector system in this case may include an interface for connecting the rechargeable battery to an external power supply. If an X-ray detector system with an X-ray detector and a dosimeter detachably coupled thereto is involved, this interface may be advantageously located in the component that is also fitted with the rechargeable battery. The interface to the power supply may be arranged on the outside of a housing of the X-ray detector system or of the relevant component (dosimeter and/or X-ray detector), such that the X-ray detector system or the relevant component can be plugged into a charging station at times when it(they) is/are not required, in order to recharge the rechargeable battery.

In a particular example embodiment, the mobile dosimeter has a housing with an insert compartment for an X-ray detector. The insert compartment can be designed, for example, such that it is possible for a conventional detector cassette with a film/foil system or storage foil system to be inserted.

The dosimeter can be designed in various ways. In an example embodiment, it has a number of ionization chambers. For example, it is possible to use a single ionization chamber that extends over a part or over the whole surface of the detector.

However, the dosimeter may be structured in order to measure the dose rate separately in different spatial regions. For example, it is possible to use three ionization chambers that are arranged in the measuring plane in a triangle standing on the apex. Consequently, the dose rates in the corner regions of the triangle can be measured exactly separately from one another.

Thus, for example, when recording the lung, the dose rates in the upper regions of the two pulmonary lobes as well as in the middle and lower regions can be determined separately such that it is possible when recording to adapt the dose exactly to the type and/or aim of the respective recording. When use is made of one ionization chamber, the latter is preferably located upstream of the X-ray detector.

In an alternative example embodiment, the dosimeter has a number of dose measuring elements with X-ray sensitive semiconductor sensors. Here, as well, it is sufficient in the simplest case to use one dose measuring element. However, a number of dose measuring elements may be used, for example, in order to build up a structured dosimeter.

In an example embodiment, a digital X-ray detector is used for the X-ray detector system. In such a detector, the image produced by the X-radiation is not picked up on a film or a storage foil, but rather a digital image that can be read out and further processed electronically is produced directly. Since the digital data must in any case be transmitted via a data communications interface to a control unit or an image data recording unit, such a mobile X-ray detector must have a suitable data communications interface.

Such an X-ray detector likewise requires a power supply unit such that the energy supply unit is also already present in the case of a mobile digital X-ray detector. It is therefore obvious for the purpose of providing a mobile X-ray detection system according to at least one embodiment of the invention to integrate the dosimeter directly with the X-ray detector in a permanent way in a housing, and to use the energy supply device and the data communications interface for both components.

An example of a digital X-ray detector the relatively novel solid state detectors that have been known for several years and are currently being introduced into the market. These X-ray detectors are based as a rule the so-called active readout matrices, for example made from amorphous silicon (a-Si).

In a variant, the X-rays containing the image information are firstly converted into light in an X-ray converter. Use is made for this purpose of, for example, an X-ray converter made from a luminescent material, for example a scintillator such as cesium iodide (CsI) or a phosphor. Alternatively, it is possible to use an X-ray converter—for example based on selenium—that generates electric charge, for example, electrons and/or holes, directly from the X-radiation.

Located downstream of the X-ray converter is an image pickup for spatially resolved measurement of the light or the electric charge generated in the X-ray converter by the X-radiation. This image pickup advantageously includes a readout matrix with individual matrix elements. If the X-ray converter converts the X-rays into light, the individual matrix elements can, for example, be designed as photodiodes in which the light is converted into electric charge and stored in the matrix elements. If the X-ray converter converts the X-radiation directly into electric charge, the matrix elements can be constructed, for example, on the basis of amorphous silicon, the matrix elements being designed as electrodes on which electric charge is stored. The charge stored in the active readout matrix can subsequently be subjected to analog/digital treatment after being read out via an active switching element with dedicated electronics and be further processed by the imaging system. Other technologies that can be used here, which finally supply digital X-ray images, are based on CCDs (Charge Coupled Devices), APS (Active Pixel Sensor) or CMOS chips, these likewise being specific forms of image pickups that are arranged in each case downstream of an appropriate X-ray converter.

In this case, the dosimeter can be integrated, for example, in the X-ray detector in such a way that it is arranged downstream of the X-ray converter in the X-ray direction. A more accurate example embodiment of this will be explained later.

In at least one example embodiment, it is ensured that the dosimeter is arranged downstream of the X-ray detector in the X-ray direction if this is permitted by the type of dosimeter. This has the advantage that the dosimeter does not influence the X-ray image or lead to artefacts. In the case of a design of an X-ray detector system as described above, having an X-ray converter and an image pickup arranged downstream thereof, and a dosimeter integrated in this X-ray detector, this means that the dosimeter is arranged not only downstream of the X-ray converter in the X-ray direction, but also downstream of the image pickup.

An X-ray detector system according to at least one embodiment of the invention can be used in conjunction with the most varied X-ray installations. In addition to an X-ray source, an X-ray generator and the other conventional components, all that is required for this by the X-ray facility is a data communications interface, appropriate to the X-ray detector system, for receiving dose data or dose rate data from the relevant X-ray detector system in order thus to form in common with the X-ray detector system according to at least one embodiment of the invention a powerful, very flexible X-ray system. If standardized interfaces are used for data transmission, it is also possible to employ a number of X-ray detector systems with one X-ray facility. It is then likewise possible to interchange the X-ray detector systems of various X-ray facilities.

BRIEF DESCRIPTION OF THE DRAWINGS

The invention is explained once again in more detail below with the aid of an example embodiment and with reference to the attached figures, in which:

FIG. 1 shows a schematic section through a first example embodiment of a mobile X-ray detector system according to the invention, FIG. 2 shows a perspective partial section through an X-ray converter layer, arranged on an active matrix, with an enlarged illustration of a photodiode matrix element with an associated switching element.

DETAILED DESCRIPTION OF THE EXAMPLE EMBODIMENTS

Figure 3:
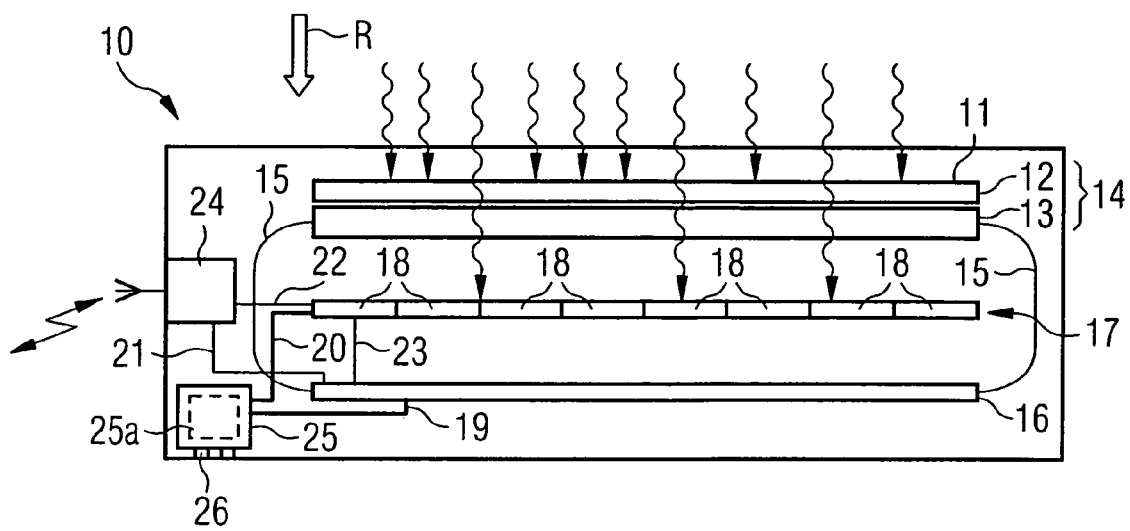
FIG. 3 shows a schematic section through a second example embodiment of a mobile X-ray detector system according to the invention, with an X-ray detector constructed in accordance with FIG. 2.

The example embodiment illustrated in FIG. 1 is a mobile X-ray detector system 1 comprising a mobile dosimeter 3 with a housing 4 into which a mobile X-ray detector 2 is inserted during operation.

For this purpose, the dosimeter 3 has a housing 4 with an insert compartment 9; a conventional film/foil cassette, for example, can be pushed as X-ray detector 2 into the compartment in an insertion direction E and withdrawn again in a withdrawal direction A. Arranged on one side in a plane in a fashion parallel to the insert compartment 9 are a number of ionization chambers 3i that serve as dose measuring elements. These ionization chambers 3i can, for example, be arranged relative to one another in the triangular shape already described above. During operation, the mobile X-ray detector system 1 formed by the dosimeter 3 and the X-ray detector 2 inserted therein is positioned such that the ionization chambers 3i are located upstream of the X-ray detector 2 in the X-ray direction R.

The ionization chambers 3i are connected to a rechargeable battery 5a via an interface 8 with the aid of an energy supply device 5, and supplied thereby with the required voltage. The energy supply device 5 has a charging interface 6 that is arranged outside on the housing 4 of the dosimeter 3 and via which the rechargeable battery 5a is charged when the dosimeter 3 is plugged into a charging station (not illustrated) during pause times.

Moreover, the interface 8 of the ionization chambers 3i is connected to a data communications interface 7 that transmits the dose rate signals measured by the ionization chambers 3i to a control unit of the X-ray installation in a wireless fashion and in a suitable form. This data communications interface 7 can have, for example, suitable amplifiers for amplifying the signals measured by the ionization chambers 3i and/or, if appropriate, also an analog/digital converter in order to transmit the data in digital form. However, these components can also already be present in the interface 8 of the ionization chamber 3i.

The data communications interface may be, for example, a radio interface. Use can be made in this case of an already known standard such as Bluetooth, W-LAN, DECT or the like. This wireless communications interface can likewise, however, also be an infrared interface or an ultrasonic interface. However, a radio interface is preferred because no visual link is required and because of the generally better transmission quality and greater range.

As an option, the dosimeter 3, for example inside the insert compartment 9, can have an interface 9s for coupling a mobile X-ray detector 2 if the latter likewise requires a power supply and/or a data communications interface. It is then possible to couple the detector 2 via this interface 9s to the energy supply device 5 and the data communications interface 7 of the dosimeter 3, and thus to achieve common use of these components 5, 7. In this case, the detector 2 has an interface 2s appropriate to the interface 9s such that contact is preferably automatically ensured between these interfaces as soon as the detector 2 is inserted into the insert compartment 9 in the insertion direction E. An example of an X-ray detector that can be designed in this way is a digital X-ray detector, for example a solid state detector.

FIG. 2 shows a schematic of a typical design of a solid state detector 14. This solid state detector 14 firstly has an image-capable X-ray conversion layer, for example made from cesium iodide, at the frontmost position in the X-ray direction R. The incoming X-radiation is converted into light in this X-ray converter 12. This light is detected by an active readout matrix 13, the actual image pickup 13, which is located directly downstream of the X-ray converter 12 and constructed, for example, on the basis of amorphous silicon, and converted into electric charge. For this purpose, the matrix 13 has a number of photodiode elements 27 that can be read out in each case via an active switching element 28, for example an integrated transistor or a diode.

In this case, the driving is performed as a rule by a row driver, which is illustrated here by the arrow 29. The reading out is performed column by column in the arrow direction 30, the outgoing signals being fed to suitable amplifiers, multiplexers and ADCs. What is concerned here is a conventional solid state detector design, from which it follows that the details with reference to the design as well as to the driving and the tripping mechanism are known to the person skilled in the art and need not be explained further.

The design principle illustrated in FIG. 1 can also be implemented in reverse when using a digital detector that is designed, for example, in the abovedescribed form and requires a power supply unit and a data communications interface for transmitting the digital data. That is to say, it is possible, for example, to integrate the solid state detector in a housing with a power supply unit and a data communications interface, and this housing has for example insert or laying-compartments or other coupling devices in order to couple the dosimeter to the detector.

FIG. 3 shows a further alternative example embodiment, in the case of which a digital X-ray detector 14 is constructed directly in a very compact fashion with a dosimeter 17 in a common housing 11 to form a mobile X-ray detector system 10.

The X-ray converter layer 12 and the active readout matrix 13 (compare FIG. 2) are located here in a housing 11 in which there is accommodated at the rear an electronics board 16 that includes the required electronics such as amplifiers, multiplexers, ADCs etc. for reading out the active matrix 13. The electronics board and the active matrix 13 are interconnected by signal lines 15. The power supply is performed via a power supply line 19 to an energy supply device 25 that is integrated in the housing 11 and has a rechargeable battery 25a. This rechargeable battery 25a can be charged in a charging station (not illustrated) via a charging interface 26.

The image data are read out, and control commands are transmitted via a control and image data line 31 to a data communications interface 24, here a radio interface 24, that transmits the data and control commands in a wireless fashion to a corresponding data communications interface of a control unit of the X-ray installation, or receives appropriate control commands therefrom.

Together with a number of dose measuring elements 18, likewise arranged in matrix form and made from an X-ray sensitive material, the X-ray dosimeter 17 is located between the active readout matrix 13 and the electronics board 16. In the present example case, this is for example a matrix arrangement of 20×20 active dose elements 18.

The X-ray component passing through the imaging system, that is to say the X-ray detector 14 formed by the X-ray converter 12 and the image pickup 13, passes to this X-ray dosimeter 17. When use is made of conventional materials for the X-ray conversion layer and the image pickup, the X-ray component passing through the X-ray detector 14 is sufficiently large for dosimetry. For example, the absorption in CsI-based conversion layers is approximately 70% given a beam quality of 70 KV and 21 mm of aluminum filtering.

In the case of selenium-based conversion layers, the absorption is only 45% given the same data. These example values are based in each case on typical layers of the relevant materials. In the event of relatively high tube voltages such as, for example, 120 KV for thorax examinations, the likelihood of absorption is even less.

A substantial portion of the X-radiation can consequently also be detected downstream of the X-ray converter. The same holds for the customary image pickup materials, that is to say the image pickup is also still transparent enough to the X-radiation—particularly when an active matrix is used. All that is required is to take account of the shielding action of the X-ray detector 14 when calculating the dose from the measured values of the dosimeter.

The incoming X-ray dose rate is measured in each case in the individual dose measuring elements 18. The individual dose elements 18 can be arranged at will in this case. For example, arrangements in the form of a chessboard or honeycomb are also possible apart from a matrix arrangement. These arrangements preferably cover the area. Depending on requirement, the individual dose measuring elements 18 can also be activated in any desired arrangement, that is to say they can be used for dosimetry. The dosimeter 12 can therefore be ideally tuned to the organ to be examined in the respective measurement.

The dose measuring elements 18 are supplied with power via a power supply line 20, which likewise leads to the power supply unit 25 arranged in the common housing 11. The readout electronics for the dose measuring elements 18 are located, in turn, on the electronics board 16, which is connected to the dosimeter 17 via a data line 23. Alternatively, the readout electronics for the dose measuring elements 18 can, however, also be integrated on a separate board in the housing 11.

The dose measuring elements 18 can, for example, be driven via a control line 22 which, in turn, leads to the data communications interface 24 that receives the control commands by radio from a system control unit of the X-ray installation. The readout dose rate data can be transmitted, in turn, via the control line 21 to the wireless communications interface 24, and from there by radio to the control unit of the X-ray installation.

Figure 4:
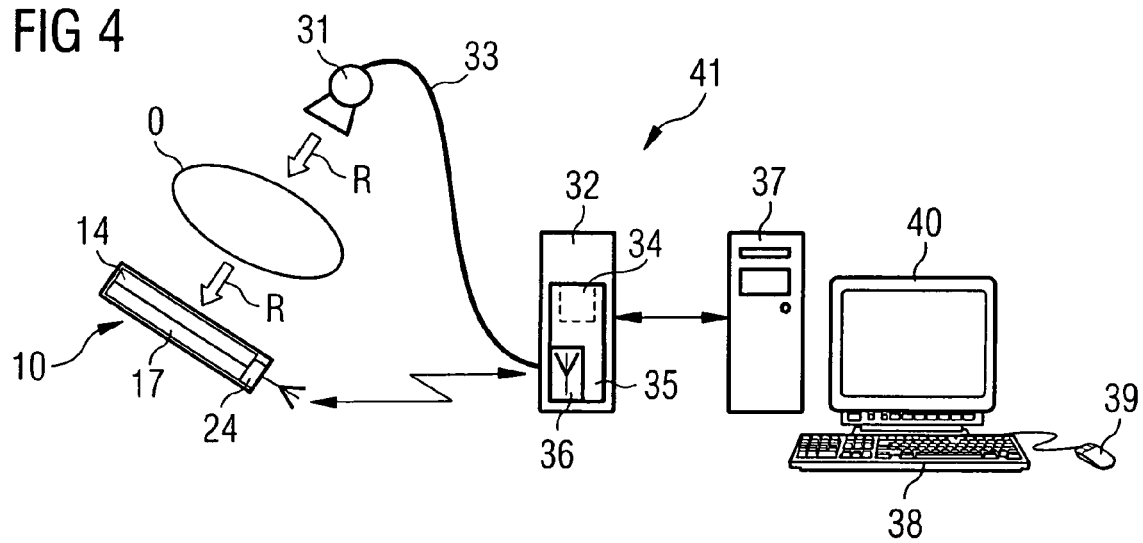
FIG. 4 shows a schematic arrangement of the components of an X-ray facility with a mobile X-ray detector system in accordance with FIG. 3.

FIG. 4 shows the use of this mobile X-ray detector system 10 with a conventional X-ray facility 41. The X-ray facility 41 has an X-ray machine 31, fastened on a machine stand (not illustrated), and an X-ray generator 32. According to at least one embodiment of the invention, the X-ray detector 10 is mobile and can be freely positioned. The positioning of the X-ray detector 10 is performed such that the examination object O, for example a specific body part of a patient, is located between the X-ray detector 10 and the X-ray machine 31. In order to reduce scattered rays, it is also possible to arranged an anti-scatter grid (not illustrated) upstream of the X-ray detector, that is to say between the examination object O and the X-ray detector system 10. Such an anti-scatter grid can also be integrated in the mobile X-ray detector or the mobile X-ray detector system 10.

The entire X-ray system is driven by a system control unit 35 that is integrated here in the X-ray generator 32 and operated in the usual way via an image computer 37 having a monitor 40, keyboard 38 and mouse 39. The X-ray machine 31 is supplied with the required high voltage from the X-ray generator 32 via a power supply line. The X-ray machine 31 is driven by the system control unit 35 via a control line. The control line and the high voltage supply line are illustrated here only schematically in the form of a common power supply and control line 33.

Located inside the system control unit 35 is a dose regulation unit 34 that can be implemented in the form of software on a computer unit of the system control unit 35. This dose regulation unit 34 is fed the dose rate values measured in the dosimeter 17 of the X-ray detection system 10. The dose regulation unit 34 can then use the measured dose rate to determine the current dose, and switch off the X-ray machine 31 when the desired dose is reached.

The dose rate values measured by the dosimeter 17 are transmitted in this case via the wireless interface 24 of the mobile X-ray detector system 10 to an appropriate wireless interface 36 that is integrated in the system control unit 35. Alternatively, this wireless interface 36 can also be present as a separate unit that is connected to the system control unit 35 via a cable.

The dosimeter 17 is also driven via this wireless interface 36. The image data can likewise be transmitted to the image computer 37 via this wireless interface 36. This image computer 37 can be used, for example, to display the images on the monitor in a desired way, to process them further or store them and/or to pass them on to other computers of the image information system.

As FIG. 4 shows, such an X-ray detector system according to at least one embodiment of the invention can also be used with conventional X-ray facilities. It is merely required that an appropriate wireless interface 36 be retrofitted in order to be able to communicate with the wireless data communications interface 24 in the mobile X-ray detector system 10.

The mobile X-ray detector system 10 in accordance with FIG. 3 was used in FIG. 4 merely as an example. However, it is also possible in principle to replace the X-ray detector system 10 by any other desired X-ray detector system according to at least one embodiment of the invention, in particular by an X-ray detector system 1 in accordance with FIG. 1.

If such a mobile X-ray detector system 1 is used with a classic film/foil detector or storage foil detector, it is, however, not necessary to transmit image data via the wireless interface. In this case, the wireless data communications interface is used only to drive the dosimeter 3. After the X-ray picture has been taken, the detector cassette 2 is then, as shown in FIG. 1, for example, taken out of the mobile dosimeter 3 and the film is developed in the usual way or the storage foil is read out and the image data are further processed.

It may be pointed out expressly once again that the design illustrated in the figures is only an example embodiment, and that it is within the discretion of the person skilled in the art to vary individual features and, in particular, also to use different combinations of the said features in order to adapt the X-ray detector according to at least one embodiment of the invention precisely to the respective intended use.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A mobile X-ray detector system, comprising:
   a mobile X-ray detector; and
   a mobile dosimeter arranged on the X-ray detector, at least during operation; wherein
      the dosimeter includes a housing with an insert compartment for detachably coupling the X-ray detector to the mobile dosimeter.

2. The X-ray detector system as claimed in claim 1, further comprising an interface for wireless data communication with a control unit.

3. The X-ray detector system as claimed in claim 1, further comprising an integrated energy supply unit.

4. The X-ray detector system as claimed in claim 3, wherein the energy supply unit includes a rechargeable battery, and wherein the X-ray detector system includes a charging interface for connecting the rechargeable battery to an external power supply.

5. The X-ray detector system as claimed in claim 1, further comprising a digital X-ray detector.

6. The X-ray detector system as claimed in claim 1, wherein the X-ray detector includes an X-ray converter for converting the X-radiation into at least one of light and electric charge, and an image pickup, arranged downstream thereof, for spatially resolved measurement of at least one of the light and the electric charge generated by X-radiation in the X-ray converter, and wherein the dosimeter is arranged downstream of the X-ray converter in the X-ray direction.

7. The X-ray detector system as claimed in claim 1, wherein the dosimeter is arranged downstream of the X-ray detector in the X-ray direction.

8. The X-ray detector system as claimed in claim 1, wherein the dosimeter includes a number of ionization chambers.

9. The X-ray detector system as claimed in claim 1, wherein the dosimeter includes a number of dose measuring elements with X-ray sensitive semiconductor sensors.

10. An X-ray facility, comprising:
    an X-ray source;
    an X-ray generator; and
    an interface for receiving at least one of dose data and dose rate data from an X-ray detector system as claimed in claim 1.

11. An X-ray system comprising an X-ray facility as claimed in claim 10.

12. A mobile dosimeter for an X-ray detector system as claimed in claim 1 comprising a coupling device for connection to an X-ray detector.

13. The dosimeter as claimed in claim 12, comprising an interface for wireless data communication with a control unit.

14. The dosimeter as claimed in claim 12, further comprising an integrated energy supply device.

15. A mobile X-ray detector for an X-ray detection system as claimed in claim 1 comprising a coupling device for connection to a mobile dosimeter.

16. The X-ray detector as claimed in claim 15, comprising an interface for wireless data communication with a control unit.

17. The X-ray detector as claimed in claim 15, comprising an integrated energy supply unit.

* * * * *